(12) United States Patent
Sumners et al.

(10) Patent No.: US 9,421,365 B2
(45) Date of Patent: Aug. 23, 2016

(54) APPARATUS FOR STIMULATING MUSCLES OF A SUBJECT AND METHOD OF PERFORMING THE SAME

(71) Applicant: Actegy Limited, Ascot, Berkshire (GB)

(72) Inventors: David Paul Sumners, Walton on Thames (GB); Katya Nikolova Mileva, London (GB)

(73) Assignee: Actegy Limited (GB)

( * ) Notice: Subject to any disclaimer, the term of this patent is extended or adjusted under 35 U.S.C. 154(b) by 0 days.

(21) Appl. No.: 14/111,893

(22) PCT Filed: Mar. 27, 2013

(86) PCT No.: PCT/GB2013/000135
§ 371 (c)(1),
(2) Date: Oct. 15, 2013

(87) PCT Pub. No.: WO2013/150257
PCT Pub. Date: Oct. 10, 2013

(65) Prior Publication Data
US 2014/0067010 A1     Mar. 6, 2014

(30) Foreign Application Priority Data
Mar. 28, 2012   (GB) .................................. 1205448.2

(51) Int. Cl.
*A61N 1/36*     (2006.01)
*A61N 1/08*     (2006.01)

(52) U.S. Cl.
CPC .............. *A61N 1/36003* (2013.01); *A61N 1/08* (2013.01); *A61N 1/36014* (2013.01)

(58) Field of Classification Search
CPC ....................... A61N 1/36003; A61N 1/36146
USPC ........................................................ 607/2, 48
See application file for complete search history.

(56) References Cited

U.S. PATENT DOCUMENTS 3,731,111 A * 5/1973 Charters ........................ 307/106
4,492,233 A * 1/1985 Petrofsky et al. ............... 607/48
(Continued)

FOREIGN PATENT DOCUMENTS

| EP | 0196393 A1 | 10/1986 |
|---|---|---|
| EP | 2260900 A1 | 12/2010 |

(Continued)

OTHER PUBLICATIONS

International Search Report, PCT App. No. PCT/GB2013/000135, mailed Jul. 26, 2013, 8 pages.
(Continued)

*Primary Examiner* — Amanda Patton
(74) *Attorney, Agent, or Firm* — Jason Saunders; Arnold, Knobloch & Saunders, L.L.P.

(57) ABSTRACT

A method of electrostimulation of the muscles of a subject is provided, the method comprising applying to the subject a plurality electrical pulses to induce contraction of at least one muscle of the subject, each pulse having a pulse width of at least 0.5 milliseconds. An apparatus for the electrostimulation of the muscles of a subject is also provided, the apparatus comprising a generator for generating a plurality of electrical pulses; means for applying the electrical pulses to the subject to induce contraction of at least one muscle of the subject; wherein the generator is operable to produce a plurality of electrical pulses each having a pulse width of at least 0.5 milliseconds.

9 Claims, 5 Drawing Sheets

(56) References Cited

U.S. PATENT DOCUMENTS

| | | | |
|---|---|---|---|
| 4,556,214 | A | 12/1985 | Pestrofsky et al. |
| 4,830,009 | A | 5/1989 | Schmitt et al. |
| 5,769,875 | A | 6/1998 | Peckham et al. |
| 2007/0270917 | A1 | 11/2007 | Nachum |
| 2008/0208288 | A1 | 8/2008 | Gesotti |
| 2009/0240304 | A1 | 9/2009 | Blum et al. |
| 2009/0319003 | A1 | 12/2009 | Castel et al. |
| 2011/0230938 | A1 | 9/2011 | Simon et al. |
| 2011/0288602 | A1 | 11/2011 | Nachum et al. |

FOREIGN PATENT DOCUMENTS

| | | |
|---|---|---|
| GB | 2136297 A | 9/1984 |
| GB | 2438589 A | 12/2007 |

OTHER PUBLICATIONS

Search Report, GB App. No. 1205448.2, Jul. 12, 2012, 2 pages.

\* cited by examiner

APPARATUS FOR STIMULATING MUSCLES OF A SUBJECT AND METHOD OF PERFORMING THE SAME

The present invention relates to a method of stimulating the muscles of a subject and to an apparatus for performing the same.

The electrical stimulation of the muscles of a subject is known in the art. Electrical stimulation of the muscles is achieved by applying one or more electrodes to the subject, typically to the skin in the region of the muscles to be stimulated. Electrical pulses are applied to the subject through the electrodes, which in turn stimulate the muscles to contract. It is known to apply electrical stimulation by means of a train of pulses having a range of different patterns, including a uniform pulse length and pulse separation.

Apparatus and devices for such electrical stimulation are known and commercially available. One such apparatus is the Circulation Booster™ available from High Tech Health Limited, UK (now Actegy Limited). The apparatus comprises an electrically conductive pad, onto which the user places a foot. Pulses of electrical current are applied to the pad, which induce the muscles in the foot and leg of the subject to contract. The pulses of electrical current may be applied in a number of different patterns and at different current levels, according to the treatment required and the condition of the subject.

Methods and apparatus for the electrical stimulation of the muscles of a subject are also known in the literature.

U.S. Pat. No. 4,528,984 discloses an autoprogrammable functional electrical stimulation apparatus and a method of operating the same. The apparatus provides the functional electrical stimulation (FES) of muscles or muscle groups of a subject by applying electrical pulses. The apparatus is manually operable to control the amplitude of the electrical pulses to provide a desired FES regime. This regime is stored in the apparatus and is reproduced by a processor, to apply the desired pulse regime to the subject.

U.S. Pat. No. 4,712,558 concerns an investigative method and apparatus for the electrical stimulation of the muscles of a subject. U.S. Pat. No. 4,712,558 discusses recording the electromyographic responses of a muscle when stimulated, for example by neural or electrical stimulation. The electromyographic responses typically include so-called motor unit action potentials or MUAPs. U.S. Pat. No. 4,712,558 reports on the investigation of MUAP discharge sequences and their analysis, in particular that the MUAP responses comprise two elements of information: first the information necessary to generate the stimulus needed for contraction of the muscle and resulting movement of joints to which the muscle is attached; and second the information for generating an intracellular environment within the muscle tissue for biosynthesis. This information is employed in U.S. Pat. No. 4,712,558 to generate an electrical signal for the artificial stimulation of the muscles of a subject. In the method of U.S. Pat. No. 4,712,558, electrical pulses are generated and applied to the subject, in particular by means of electrodes overlying the skin of the subject, the intervals between respective stimulating pulses being capable of being individually defined or varied.

In a further development of U.S. Pat. No. 4,712,558, U.S. Pat. No. 5,350,415 describes a method and apparatus for the trophic stimulation of muscles. The stimulation is achieved by applying a pattern of electrical pulses to the muscles of the subject, as in U.S. Pat. No. 4,712,558. U.S. Pat. No. 5,350,415 describes the application of sampled predictive running average analysis of the MUAP signals to generate a pulse sequence for electrical stimulation of muscle tissue. In particular, U.S. Pat. No. 5,350,415 discloses the generation of a pulse sequence having a continuous low-rate firing activity, described mathematically as a delta function continuously pulsing at a slow base rate with interpulse intervals in the range of from 120 to 200 milliseconds. This pattern has superimposed thereon a rectangular-like modulation with an exponential rise and fall, which quickly (that is within 20 to 40 milliseconds) changes the low base rate into a burst of high rate short pulses having a short interpulse interval (IPI) of from 20 to 40 milliseconds. The decrease in the IPI is maintained for about 40 milliseconds, that is for about three to four pulses, after which it is reduced exponentially to an IPI of from 60 to 80 milliseconds. Finally, after about 500 milliseconds, the IPI is further decreased to a base slow rate of 120 to 200 milliseconds. The entire cycle has a recurrence period of about 1 second. The train of electrical pulses having the aforementioned pattern is applied to the subject to stimulate the muscle activity.

More recently, WO 2008/086411 discloses an electrostimulation device to provoke the venous pumping of blood from the legs of a subject. The venous blood pumping is induced by applying to the subject short bursts of electrical impulses of high energy at a predetermined durational range, in which each burst has an associated modulated intensity and/or time duration. Particular pulse regimes disclosed in which pulses are spaced by intervals of 4 milliseconds. Superimposed on these pulses is a modulation pattern, in which the width of the pulses is first increased, to provide increasing energy applied to the subject, and thereafter decreased to reduce the energy being applied in each pulse. The impulse width of the high energy pulses is indicated to range from 26 to 240 microseconds. A so-called 'minimal energy' phase then follows, during which low energy pulses are applied, the low energy pulses having insufficient energy to stimulate contractions of the muscles. The pulse width of the low energy pulses is from 400 to 900 milliseconds. The low energy pulses are indicated to provide an electroanesthetization of the subject.

US 2011/0288602 discloses a non-invasive method and device form promoting localised changes in blood flow through the blood vessels of a limb. The device applies electrical stimulation to the tissue by way of three separate electrodes, so as to induce muscle contraction. A similar method and device are disclosed in US 2007/0270917.

GB 2 136 297 concerns the electronic stimulation of muscles and employs an electrode harness for stimulating bodily movements in a human patient. A train of electrical pulses is applied to the patient through the harness. The voltage and spacing of the pulses in the pulse may be varied.

US 2011/0230938 discloses a device for the non-invasive electrical stimulation. The device is configured to produce a peak voltage to generate an electric field in the region of a target nerve sufficient to produce a physiological effect, without substantially stimulating other nerves lying between the target nerve and the skin of the subject.

U.S. Pat. No. 4,830,009 discloses a method and apparatus for the treatment of scoliosis by means of electrical stimulation.

A pulse generator for providing electrical pulses to a subject to relieve muscle spasm is disclosed in U.S. Pat. No. 3,731,111.

Finally, a method and apparatus for stimulating cell initiated nitric oxide (NO) activation, interstitial protein clearance and angiogenesis are disclosed in US 2009/0240304.

While much work has been devoted to developing systems and methods for the electrostimulation of a subject's muscles, there is still a need for an improved system and method.

It has now been found that narrow pulse widths as applied in prior art electrostimulation methods recruit the sensory system of the subject to a low level. It has further been found that electrical pulses with a greater width, that is duration, recruit the subject's sensory system more. This, in turn, generates a muscle contraction in the subject more closely representing the voluntary contractions of the subject's muscles. This reduces premature fatigue in the muscles of the subject, an effect usually associated with stimulation using a pattern of narrow pulses. A further advantage of the greater pulse width is that the current level required to be delivered to the subject to produce a given increase in the blood flow of the subject can be reduced. Overall, this improves the efficacy of the electrostimulation treatment and reduces the discomfort of the subject.

Accordingly, in a first aspect, the present invention provides a method of electrostimulation of the muscles of a subject, the method comprising applying to the subject a plurality electrical pulses to induce contraction of at least one muscle of the subject, each pulse having a pulse width of at least 0.5 milliseconds.

In a further aspect, the present invention provides an apparatus for the electrostimulation of the muscles of a subject, the apparatus comprising:

a generator for generating a plurality of electrical pulses;

means for applying the electrical pulses to the subject to induce contraction of at least one muscle of the subject;

wherein the generator is operable to produce a plurality of electrical pulses each having a pulse width of at least 0.5 milliseconds.

The present invention provides an electrostimulation to the subject, by way of applying to the subject a series of electrical pulses to induce a plurality of contractions in one or more muscles of the subject. The method of the present invention finds particular use in increasing blood flow in a range of vascular vessels, including the large blood vessels (arteries and veins) and the small blood vessels (tissue capillaries) of the subject. The method finds particular use in increasing the flow of blood in the feet and legs of the subject.

The electrical pulses are applied to the subject in a manner appropriate to stimulate the action of the muscle or muscle group being targeted. The electrical pulses may be applied using any suitable means. For example, the electrical pulses may be applied percutaneously to the subject, in particular by electrodes extending into the skin of the subject. More preferably, the electrical pulses are applied transcutaneously by means of electrodes or other electrical contact means applied to the skin of the subject.

In one embodiment of the invention, to induce venous blood flow, in particular the venous return, in the legs of the subject, the electrical pulses are applied to one or both feet of the subject, more preferably to the soles of one or both feet. A preferred embodiment of an apparatus for applying the electrostimulation to a subject is described in more detail hereinbelow.

The present invention applies a series or train of electrical pulses to the subject, in order to induce contractions in one or more muscles of the subject. In terms of the present invention, the term 'pulse' is a reference to an electrical pulse with a current and voltage varying between a low level, at which contraction of the muscle of the subject is not induced, to a high level at which muscle contraction occurs. The low level is any suitable level that does not induce muscle contraction, for example zero. The high levels of voltage and current are as described in more detail below.

The electrical pulses are so-called 'wide pulses', that is are of a longer duration compared with those of the prior art. In particular, the electrical pulses of the present invention have a duration of greater than 0.5 milliseconds. Preferably, the pulses have a duration of greater than 0.75 milliseconds, more preferably at least 0.85 milliseconds. By applying pulses having a minimum pulse width as aforementioned, it has been found that the contractions induced in the muscles of the subject more closely correspond to natural or voluntary muscle contractions performed by the subject themselves. This in turn results in a significantly improved action of the muscles in pumping blood through the muscle vasculature and the venous blood vessels. Further, it has been found that, by more closely reproducing natural muscle contractions, the electrostimulation is less fatiguing for the subject. It has also been found that a desired increase in blood flow can be achieved at lower current levels than the prior art.

Excessive pulse widths should be avoided, as such electrical pulses can produce a strong bi-directional activation of motor axons. This will reduce the efficiency of the voluntary command through antidromic block of the motor nerves. This, in turn can result in a more rapid fatiguing of the muscles. In particular, the antidromic block will produce a reduced muscle contraction, similar to that produced by narrow pulse widths, resulting in an earlier onset of fatigue in the muscle, despite producing weaker contractions. Accordingly, it is preferred that the electrical pulses applied to the subject have a maximum width of 2 milliseconds, more preferably 1.75 milliseconds, still more preferably 1.5 milliseconds.

A pulse width in the range of from 0.5 to 2.0 milliseconds has been found to be advantageous, preferably from 0.6 to 1.8 milliseconds, more preferably from 0.7 to 1.75 milliseconds, still more preferably from 0.75 to 1.6 milliseconds. A pulse width in the range of from 0.75 to 1.5 milliseconds is particularly suitable, preferably from 0.8 to 1.4, still more preferably from 0.85 to 1.3 milliseconds.

It has been found that a pulse width of from 0.9 to 1.2 milliseconds is particularly advantageous, more preferably from 0.95 to 1.1 milliseconds. A pulse width of about 1.0 milliseconds is a particularly preferred embodiment of the present invention.

The electrical pulses may be applied in any suitable pattern. It is preferred that the pulses are applied with suitable rest periods between pulses or groups of pulses. For example, the pulses may be applied singly, with consecutive pulses being separated by an inter-pulse rest period. The rest period between pulses is a period in which the intensity of the electrical stimulation being applied to the subject is below the level necessary to induce contraction of the target muscle or muscles. Preferably, zero electrical stimulation is applied to the subject during the rest period.

The length of the inter-pulse rest period may be determined, at least in part, by the limitations of the apparatus being used to generate the pulses. The inter-pulse rest period may range from 50 microseconds to 250 microseconds, preferably from 60 to 200 microseconds, more preferably from 65 to 180 microseconds, still more preferably from 75 to 150 microseconds. An inter-pulse rest period of from 80 to 140 microseconds is particularly suitable, more preferably from 85 to 130 microseconds, still more preferably from 90 to 125 microseconds. An inter-pulse rest period of at least 100 microseconds is particularly preferred, for ease of construction and operation of the pulse generating apparatus.

More preferably, the pulses are applied in groups, each group comprising two or more pulses separated by a first inter-pulse rest period. Consecutive groups of pulses are separated by a second inter-pulse rest period. The second inter-pulse rest period is preferably longer than the first inter-pulse rest period.

The length of the first inter-pulse rest period may be determined, at least in part, by the limitations of the apparatus being used to generate the pulses. The first inter-pulse rest period may range from 50 microseconds to 250 microseconds, preferably from 60 to 200 microseconds, more preferably from 65 to 180 microseconds, still more preferably from 75 to 150 microseconds. A first inter-pulse rest period of from 80 to 140 microseconds is particularly suitable, more preferably from 85 to 130 microseconds, still more preferably from 90 to 125 microseconds. A first inter-pulse rest period of at least 100 microseconds is particularly preferred, for ease of construction and operation of the pulse generating apparatus.

The second inter-pulse rest period is the period of rest between successive groups of pulses. This rest period is preferably a sufficient length of time to allow the vasculature in the region being treated to refill with blood, in advance of the following muscle contraction. By allowing a sufficient rest period to substantially or wholly refill with oxygenated blood, the muscle fatigue is delayed and, as a result, the efficiency of the treatment in expelling and pumping blood is increased. The second inter-pulse rest period is preferably at least 10 milliseconds, more preferably at least 20 milliseconds, still more preferably at least 25 milliseconds. Details of a preferred rest period between pulses or groups of pulses inducing contraction in the muscles of the subject are described in more detail hereinbelow.

The ratio of each electrical pulse or group of pulses to the intervening rest period is preferably from 1:1 to 1:8, more preferably from 1:1 to 1:6, still more preferably from 1:1 to 1:4.

The train of pulses may be considered to have a duty cycle, that is the fraction of the total elapsed time of the train during which the pulses have an intensity sufficient to stimulate muscle contraction. The duty cycle may range from 5% to 75%, more preferably from 10% to 60%, still more preferably from 20% to 50%.

The groups of pulses may contain the same number of pulses or a different number of pulses. Preferably, the pulses are applied in a plurality of groups, each group having the same number of pulses therein.

Each group of pulses preferably comprises at least two pulses, more preferably at least three pulses. Higher numbers of pulses may be applied in each group, for example four pulses, five pulses, up to ten pulses. However, a high number of pulses in a given group can reduce the efficiency of the electrostimulation in inducing pumping of blood from the venous blood vessels, as the subject is provided with insufficient rest periods to allow the veins to refill with blood. Accordingly, it is preferred that the number of pulses in each group is less than ten, more preferably less than eight, still more preferably less than six. A group of less than five pulses is preferred, with pulses being arranged in groups of three or triplets being particularly preferred.

As noted, the pulses may be provided in groups of pulses. These groups of pulses may, in turn, be grouped together, such that a train of pulses comprises a plurality of groups of pulses, each of the groups comprising a plurality of sub-groups of pulses, with each of the sub-groups of pulses comprises a plurality of individual pulses. As noted, the individual pulses within each sub-group are separated by a first rest period and successive sub-groups are separate by a second rest period. Successive groups of pulses may be separated by a third rest period. The third rest period is preferably longer than the first rest period and the second rest period. The third rest period may have a duration of up to 4 seconds, preferably up to 3 seconds, more preferably up to 2 seconds.

The current level of the electrical pulses may be varied and selected to provide the desired level of muscle contraction, without being painful or unacceptably uncomfortable to the subject. Factors affecting the current level to be applied include the condition of the subject and their muscles and the resistance of the skin or tissue of the subject to which the electrical pulses are being applied. The current level will also determine the stimulation intensity of the treatment. Typical peak current levels are in the range of from 1 to 50 mA, more preferably from 5 to 40 mA, still more preferably from 10 to 30 mA.

Similarly, the voltage level to be applied will depend upon the prevailing conditions, such as the condition of the subject, the resistance of the skin or tissue of the subject and the stimulation intensity to be achieved. For a healthy subject, a typical skin resistance is from 1 to 10 kOhms, and may be lower if the skin is wet. In light of this, a typical peak voltage for the pulses is from 20 to 160 V, more preferably from 25 to 150 V, still more preferably from 30 to 140 V. A peak voltage of up to 250 V may be applied, depending upon the intensity of the stimulation to be delivered to the muscles of the subject, with peak voltages of up to 150 V being more typical for many subjects.

The pulses may be applied with voltage of a single polarity. Alternatively, pulses may be applied with an alternating polarity. The polarity of the voltage may alternate between consecutive single pulses or between consecutive groups of pulses.

The stimulation intensity of the electrostimulation may be indicated in terms of the percentage of the maximum voluntary muscle contraction achievable by the subject. A minimum stimulation intensity is 10%, more preferably at least 15%, still more preferably at least 20%. A stronger stimulation intensity may be applied, so as to induce a stronger muscle contraction. Accordingly, a stimulation intensity of up to 50%, more preferably up to 50% may be applied. A stimulation intensity in excess of 50% should preferably be avoided as this generally induces a rapid onset of muscle fatigue in the subject, reducing the efficacy of the electrostimulation session.

The electrostimulation may be applied by way of pulses of any suitable shape. For example, the variation of the voltage with time of each pulse may be in the form of a square wave. More preferably, the amplitude of the waveform of the pulses is modulated. Modulation of the pulses waveform is advantageous as it reduces the tendency for habituation of the muscles subject, whereby the response of the muscles to the electrical stimulation reduces over time. Any suitable signal may be applied to the pulses to modulate the amplitude of the waveform. Preferably, the modulation is achieved by applying a triangular signal or, more preferably, by applying a sine wave to the basic pulse waveform. The frequency of the modulation signal applied to the basic pulse waveform may vary, but is preferably from 0.5 to 2 Hz. Modulation frequencies of up to 4 Hz may be applied.

The depth of the modulation signal, that is the extent to which the amplitude of the basic waveform is varied, is preferably from 10 to 60%, more preferably from 15 to 50%.

The electrostimulation of the present invention may be applied for any suitable length of time to achieve the desired level of pumping of blood from the veins of the subject, while avoiding excessive muscle fatigue. The electrostimulation is preferably applied for a period of at least 5 minutes, more preferably at least 10 minutes. The maximum length of an electrostimulation session will be determined by such factors as the condition of the subject and the onset of muscle fatigue. Typically, the electrostimulation session is up to 40 minutes in length, more preferably up to 30 minutes in length. A session time of from 15 to 25 minutes, more preferably about 20 minutes is advantageous.

To avoid habituation of the muscles of the subject, it is preferred that the pattern of pulses, in terms of pulse duration, the rest period between pulses, the number of pulses in each group of pulses, the modulation waveform applied to the pulses, and the rest period between groups of pulses is varied throughout the session. Preferably, a given pattern or train of pulses is repeated no more than four times, more preferably no more than three times, still more preferably no more than twice in any session. In one preferred embodiment, a given train of pulses is repeated no more than twice in any 20 minutes of electrostimulation.

As described hereinbefore, it is important to provide the muscles of the subject with a rest period between successive electrical pulses or groups of pulses. As noted, the muscle is being induced to contract by electrical pulse stimulation, in order to expel blood from the venous blood vessels. In particular, the muscle is contracting under the effects of the stimulation to pump blood against the hydrostatic forces back into the central circulation system of the subject and, ultimately to the heart. After blood has been expelled from the blood vessels by the muscle contractions, there needs to follow a period of relaxation, during which the blood vessels, such as the veins, can refill with blood, before the next contraction. If insufficient time is allowed for the blood vessels to refill with blood, the muscles will generally fatigue more rapidly and subsequent muscle contractions will be less efficient in expelling and pumping blood.

Further, a sufficient rest period between muscle contractions is required for optimising muscle performance. The efficiency of muscle contractions depends both on the metabolism of the subject and the ability of the nerves and muscle fibres of the subject to be excited by stimulation. After single contractions, muscles tend to relax relatively quickly, that is within a period of 100 to 200 milliseconds. However, after repetitive contractions, either voluntary or invoked by external stimulation, a longer period is required to allow the muscle to fully relax. This period can be up to 1 second in length.

The energy for muscle contractions is derived by the muscle tissue from oxygen and macronutrients provided to the muscle by means of the arterial blood flow in the subject. A lack of sufficient oxygen and/or glycogen available to the muscles results in a rapid fatiguing of the muscles. Further, an accumulation of metabolites, such as lactate, can also enhance muscle fatigue in the subject. As a result, the efficient removal of metabolites by the venous blood flow is important in maintaining muscle performance. Therefore, repeated muscle contractions that have a rhythm falling within the rate of breathing of the subject, that is from 5 to 50 breaths per minute, and within the normal range of heart rates, that is from 50 to 150 beats per minute, will reduce premature fatigue of the muscles and will assist in maintaining an efficient and prolonged muscle pump function.

Depending upon the intensity of preceding muscle contractions, energy reserves for the muscle can be restored by nutrients supplied through the flow of arterial blood within a period of from 30 seconds to 5 minutes. It is not necessary to apply a rest period for this length of time and achieve full recovery of the muscles being stimulated. However, some rest will be required to maintain muscle performance in pumping blood through the venous system.

It has been found that the efficiency of the muscle contractions induced by electrostimulation can be maintained if the muscles are allowed to rest for a period of at least 1 second, during which the muscles of the subject being stimulated are allowed to relax.

Accordingly, in a further aspect, the present invention provides a method of electrostimulation of the muscles of a subject, the method comprising applying to the subject a plurality electrical pulses to induce contraction of at least one muscle of the subject, the electrical pulses being applied to the subject in pattern comprising a rest period between successive pulses, the rest period being at least 1 second in length.

In a further aspect, the present invention provides an apparatus for the electrostimulation of the muscles of a subject, the apparatus comprising:

a generator for generating a plurality of electrical pulses;

means for applying the electrical pulses to the subject to induce contraction of at least one muscle of the subject;

wherein the generator is operable to produce a plurality of electrical pulses, successive pulses being separated by a rest period of at least 1.0 second in length.

The pulses may be applied singularly or in groups, as described hereinbefore. If the pulses are applied singularly, a rest period of at least 1.0 second is applied between successive individual pulses.

More preferably, the pulses are applied in groups, each group comprising two or more pulses separated by a first inter-pulse rest period. In such an embodiment, the aforementioned rest period between successive pulses is a reference to a rest period between successive groups of pulses. That is, consecutive groups of pulses are separated by a second inter-pulse rest period of at least 1.0 second. The second inter-pulse rest period is preferably longer than the first inter-pulse rest period.

As described hereinbefore, the first inter-pulse rest period may range from 50 microseconds to 250 microseconds, preferably from 60 to 200 microseconds, more preferably from 65 to 180 microseconds, still more preferably from 75 to 150 microseconds. A first inter-pulse rest period of from 80 to 140 microseconds is particularly suitable, more preferably from 85 to 130 microseconds, still more preferably from 90 to 125 microseconds. A first inter-pulse rest period of about 100 microseconds is particularly preferred.

The second inter-pulse rest period is the period of rest between successive groups of pulses and is at least 1.0 second in length in this aspect of the present invention.

The ratio of the period of electrical stimulation, that is each electrical pulse or group of pulses, to the intervening rest period is preferably from 1:1 to 1:8, more preferably from 1:1 to 1:6, still more preferably from 1:1 to 1:4.

In one preferred embodiment, the ratio of the period of electrical stimulation to the rest period is about 1:1.

The duration of the rest period and the ratio of the rest period to the period of stimulation of the muscles will vary according to such factors as the condition of the muscles of the subject, the recent activity of the muscles, the metabolism of the subject, and the health of the subject.

The rest period is at least 1.0 second, to allow the venous blood vessels to fill with blood and to provide sufficient time for the muscles being stimulated to relax and recover to a sufficient level to maintain sufficient efficiency in pumping blood from the veins. The rest period may be up to 5.0 seconds, more preferably up to 4.0 seconds, still more preferably up to 3.0 seconds. In many cases, a rest period of from 1.0 to 2.0 seconds is appropriate, more preferably from 1.0 to 1.5 seconds. A rest period of about 1.0 second has been found to be suitable for the stimulation of many subjects.

Other aspects of the pulses, their grouping and their parameters are as hereinbefore described.

The apparatus for providing the electrostimulation of the present invention to a subject generally comprises the following components, which will be known to the person skilled in the art.

The apparatus comprises means for providing an electrical stimulation cycle to the subject. The means for providing the electrical stimulation may be any suitable means for generating the electrical current and supplying the current to the subject. Suitable means are known in the art.

One system for providing electrical stimulation to the subject comprises a power supply unit for providing a supply to electricity. The power supply unit may be any suitable supply unit, preferably one connectable to a domestic electrical supply. The system may further comprise a processor for operating control electronics for providing a voltage. This in turn is provided to a transformer to step the voltage up to a level suitable for administering to the subject. The processor further operates a pulse control circuit, for generating electrical pulses of the required shape and duration.

The apparatus comprises means for delivering the electrical pulses to the subject. The electrical stimulation pulses may be applied to the subject in any suitable manner. For example, the pulses may be applied percutaneously, by way of one or more electrodes extending into the skin of the subject. More preferably, the apparatus comprises one or more contact members having a contact surface for location on the skin of the subject. In this way, the electrical pulses are delivered to the surface of the skin of the subject in the region of the muscles to be stimulated.

The means for delivering the electrical pulses to the subject is provided with a first portion connected to the electrically positive side of the system and a second portion connected to the electrically negative side of the system.

The method of the present invention may be employed to provide electrical stimulation pulses to the muscles in any part of the subject. In a particularly preferred embodiment, the method and apparatus are employed to provide electrical stimulation to the muscles of the legs of the subject, in particular the lower leg, more particularly the calves, ankle and foot of the subject. Accordingly, a particularly preferred embodiment is to provide the electrical pulses to the soles of either one or both feet of the subject.

In this embodiment of the present invention, a train of electrical stimulation pulses is applied to the foot of the subject. In particular, an electrical current is applied to the plantar surface of the foot, thereby stimulating the plantar muscles of the foot and the muscles of the leg of the subject, in particular the lower leg. The electrical stimulation pulses are applied to the plantar surface of the foot through a contact member having a contact surface. The subject places their foot on the contact member of the apparatus such that the plantar surface of the foot is in contact with the contact surface. The contact surface is electrically conductive, allowing an electrical current to be provided to the plantar muscles of the foot from the apparatus. A contact surface may be applied to one foot of the subject or a contact surface may be applied to each of both feet. One preferred arrangement has a contact surface provided for each foot of the subject, with the contact surfaces being spaced apart, with electrical stimulation being applied to the subject only when both feet of the subject are in contact with their respective contact surfaces.

The contact surface may have any suitable shape, so as to provide a sufficient contact with the plantar surface of the foot of the subject. Preferably, the contact surface is elongate, having a proximal end, disposed towards the user when in use, and a distal end opposite the proximal end. More preferably the contact surface is of a size and shape to accommodate the major portion of the plantar surface of the foot. It is particularly preferred for the contact surface to be of a sufficient size to accommodate the entire underside of the foot of the subject.

The contact surface may be formed from any suitable material that conducts the electrical current to the plantar surface of the foot of the subject. For example, the contact surface may be formed from a rubber composition comprising carbon, the carbon being present in sufficient amount to provide the requisite electrical conductivity. Alternatively, the contact surface may be formed from metal or from a plastic composition that is electrically conductive or provided with an electrically conductive coating. Other suitable materials for forming the contact member and the contact surface are known in the art.

The contact surface may be flat or substantially flat. Alternatively, the contact surface may be contoured to accommodate the contours of the plantar surface of the foot of the subject. In one embodiment, the contact surface is provided with one or more ridges thereon, the electrical current being provided to the ridges of the contact surface for conducting to the foot of the subject. Alternatively, the contact surface may be smooth or substantially smooth.

Embodiments of the present invention will now be described, by way of example only, having reference to the accompanying drawings, in which.

Figure 1:
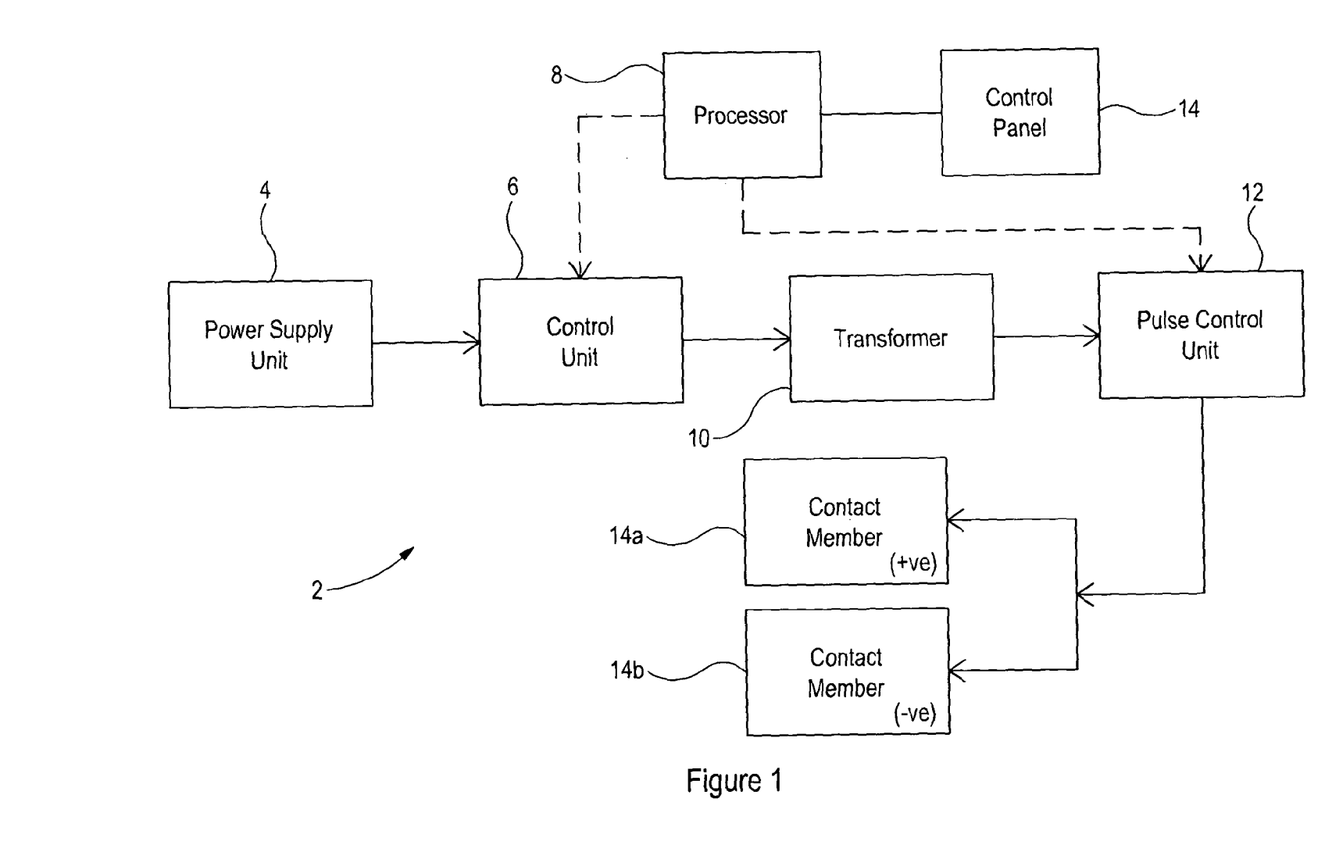
FIG. 1 is a schematic diagram of one embodiment of a system for generating electrical pulses for use in the apparatus of the present invention.

Referring to FIG. 1, there is shown a schematic diagram of one embodiment of a system for generating electrical pulses for the stimulation of the feet of a subject. The system, generally indicated as 2, is suitable for use in the method of the present invention. The system 2 is arranged for providing electrical stimulation to the plantar surfaces of the feet of a subject. However, the general aspects of the system may be used to provide electrical stimulation to muscles in other parts of the subject in like manner as described below.

The system 2 comprises a power supply unit 4, for example connectable to an electrical power supply, such as a domestic electrical supply. The power supply unit 4 outputs an electric current, the voltage of which is adjusted, as required by a control unit 6, under the action of a processor 8. The adjusted voltage is stepped up by a transformer 10, before being fed to a pulse control unit 12, also operated by the processor 8. The pulse control unit generates a pulsed electrical signal having the desired pulse shape and duration, under the action of the processor. The output of the pulse control unit 12 is connected to the first and second contact members 14a, 14b of the apparatus of FIG. 1. A control panel 14 provides a user interface for controlling the processor 8.

In use, by placing their feet on the contact surfaces of the contact members 14a, 14b, the user completes an electrical circuit, allowing the pulsed electrical signal to travel from one foot to the other and stimulate muscle contraction in the feet and legs of the user.

Figure 2:
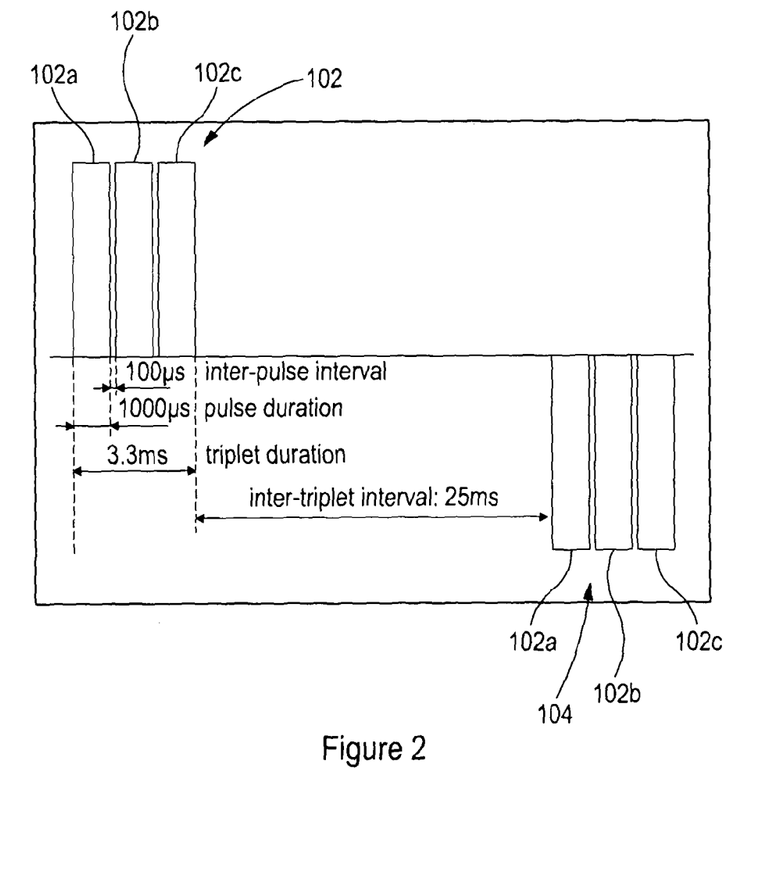
FIG. 2 is a graphical representation of a cycle of electrostimulation pulses according to a first embodiment of the present invention.

Referring to FIG. 2, there is shown a graphical representation of a train of electrical pulses for applying to a subject to stimulate contraction of a target group of muscles, such as those of the lower leg. The pulses are represented as plots of voltage against time. The train of pulses represented in FIG. 2 comprises a first group of pulses 102, comprising three pulses 102a, 102b and 102c, and a second group of pulses 104, comprising three pulses 104a, 104b and 104c. As can be seen, the pulses in the first group 102 are in the opposite polarity to those of the second group 104.

The pulses in the first and second groups 102, 104 are generally square in form, having a rapid increase in voltage from zero to a single nominal voltage between 70 and 120 V, which is held for substantially the entire duration of the pulse, after which the voltage is rapidly decreased to zero. Peak voltages of up to 250 V may be applied, depending upon the intensity of the stimulation to be applied to the subject, more typically in many cases up to 150 V.

As indicated in FIG. 2, each pulse has a width, that is a duration, of 1.0 millisecond. The pulses in each group are separated by a first inter-pulse rest period of 100 microseconds. As also shown in FIG. 2, the first group 102 and the second group 104 are separated by a second rest period. In this embodiment, the second reset period between successive groups of pulses is 25.0 milliseconds.

The train of pulses represented in FIG. 2 are operated at a duty cycle of from 20 to 50%.

The pulse train shown in FIG. 2 is repeatedly applied to the subject, as described above, during a treatment session.

Figure 3:
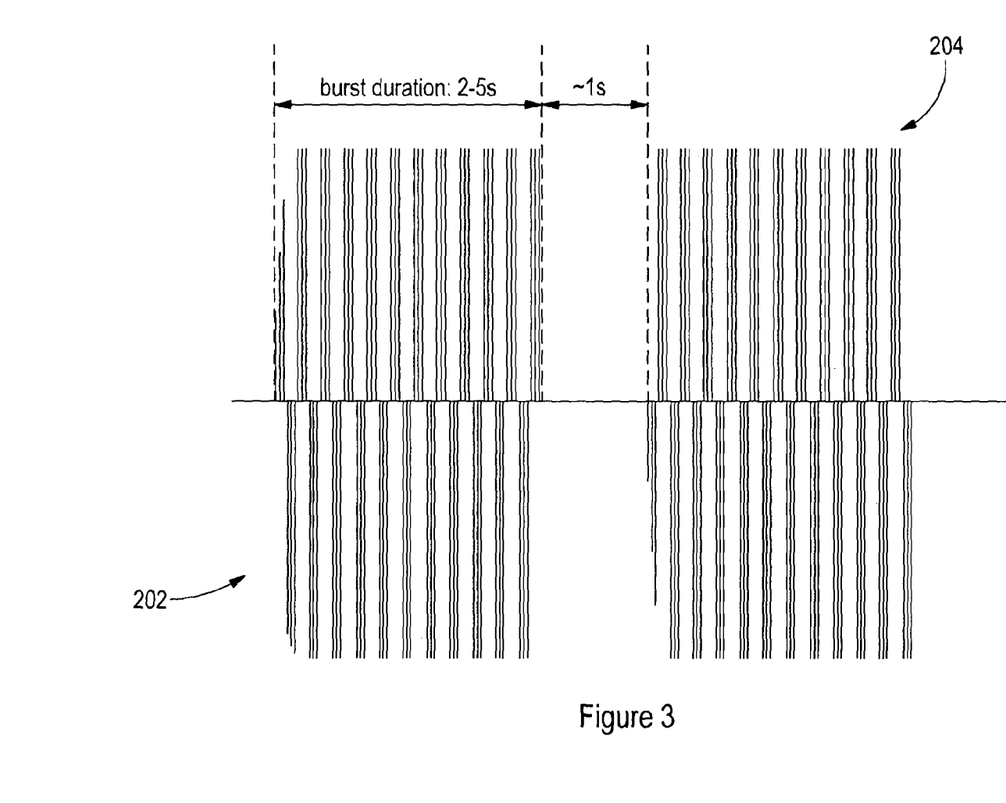
FIG. 3 is a graphical representation of a cycle of electrostimulation pulses according to a second embodiment of the present invention.

Turning to FIG. 3, there is shown a graphical representation of a train of electrical pulses for applying to a subject to stimulate contraction of a target group of muscles, such as those of the lower leg. The pulses are represented as plots of voltage against time. The train of pulses represented in FIG. 3 comprises a first group of pulses 202 and a second group of pulses 204. The pulses shown in FIG. 3 are generally square without amplitude modulation, as applied in some embodiments (described in more detail hereinbelow). The pulses in each of the first and second groups 202, 204 are arranged into sub-groups, each sub-group having three individual pulses therein. As can be seen, the sub-groups of pulses are arranged with alternating polarity.

The individual pulses in the first and second groups 202, 204 are generally square in form, having a rapid increase in voltage from zero to a single nominal voltage between 70 and 120 V, which is held for substantially the entire duration of the pulse, after which the voltage is rapidly decreased to zero. Peak voltages of up to 250 V may be applied, depending upon the intensity of the stimulation to be applied to the subject, with peak voltages of up to 150 V being applicable in many cases.

Each pulse has a width, that is a duration, of 1.0 millisecond. The pulses within each sub-group are separated by a first inter-pulse rest period of 100 microseconds.

Further, successive sub-groups of pulses are separated by a second rest period. The second rest period is 25 milliseconds.

As shown in FIG. 3, the first group 202 and the second group 204 are separated by a third rest period. In this embodiment, the third rest period between successive groups of pulses is up to 2.0 seconds, for example about 1.0 second.

The train of pulses represented in FIG. 3 are operated at a duty cycle of from 20 to 50%.

The pulse train shown in FIG. 3 is repeatedly applied to the subject, as described above, during a treatment session.

Figure 4:
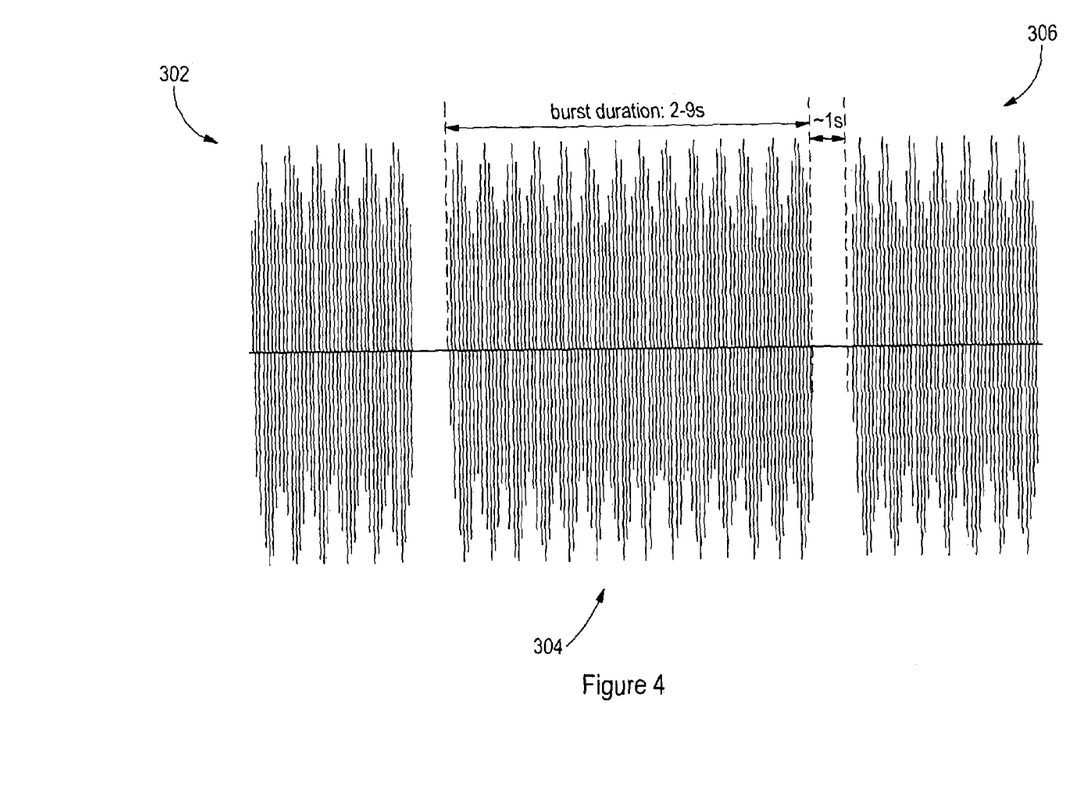
FIG. 4 is a graphical representation of a cycle of electrostimulation pulses according to a first embodiment of the present invention.

Turning to FIG. 4, there is shown a graphical representation of an alternative train of electrical pulses for applying to a subject to stimulate contraction of a target group of muscles, such as those of the lower leg. The pulses are represented as plots of voltage against time. The train of pulses represented in FIG. 4 comprises a first group of pulses 302 and a second group of pulses 304. The pulses in each of the first and second groups 302, 304 are arranged into sub-groups, each sub-group having a plurality of individual pulses therein. As can be seen, the sub-groups of pulses are arranged with alternating polarity, in particular each triplet of pulses is followed by a 25 millisecond interval, after which the triplet of pulses is repeated with the opposite polarity.

The individual pulses in the first and second groups 302, 304 are generally square in form, having a rapid increase in voltage from zero to a nominal voltage between 70 and 120 V, which is held for substantially the entire duration of the pulse, after which the voltage is rapidly decreased to zero. Peak voltages of up to 250 V may be applied, depending upon the intensity of the stimulation to be applied to the subject.

A sine wave voltage signal, the frequency of which varies from 0.5 to 4.0 Hz, is applied to modulate the peak voltage of the individual pulses, as shown in FIG. 4. The modulation depth in the amplitude of the peak voltage of each pulse as shown in FIG. 4 is about 40%.

Each pulse has a width, that is a duration, of 1.0 millisecond. The pulses within each sub-group are separated by a first inter-pulse rest period of 100 microseconds.

Further, successive sub-groups of pulses are separated by a second rest period. The second rest period is 25 milliseconds.

As shown in FIG. 4, the first group 302 and the second group 304 are separated by a third rest period. In this embodiment, the third reset period between successive groups of pulses may be up to 4.0 seconds, preferably about 1.0 second.

The train of pulses represented in FIG. 4 are operated at a duty cycle of from 20 to 50%.

The pulse train shown in FIG. 4 is repeatedly applied to the subject, as described above, during a treatment session.

Figure 5:
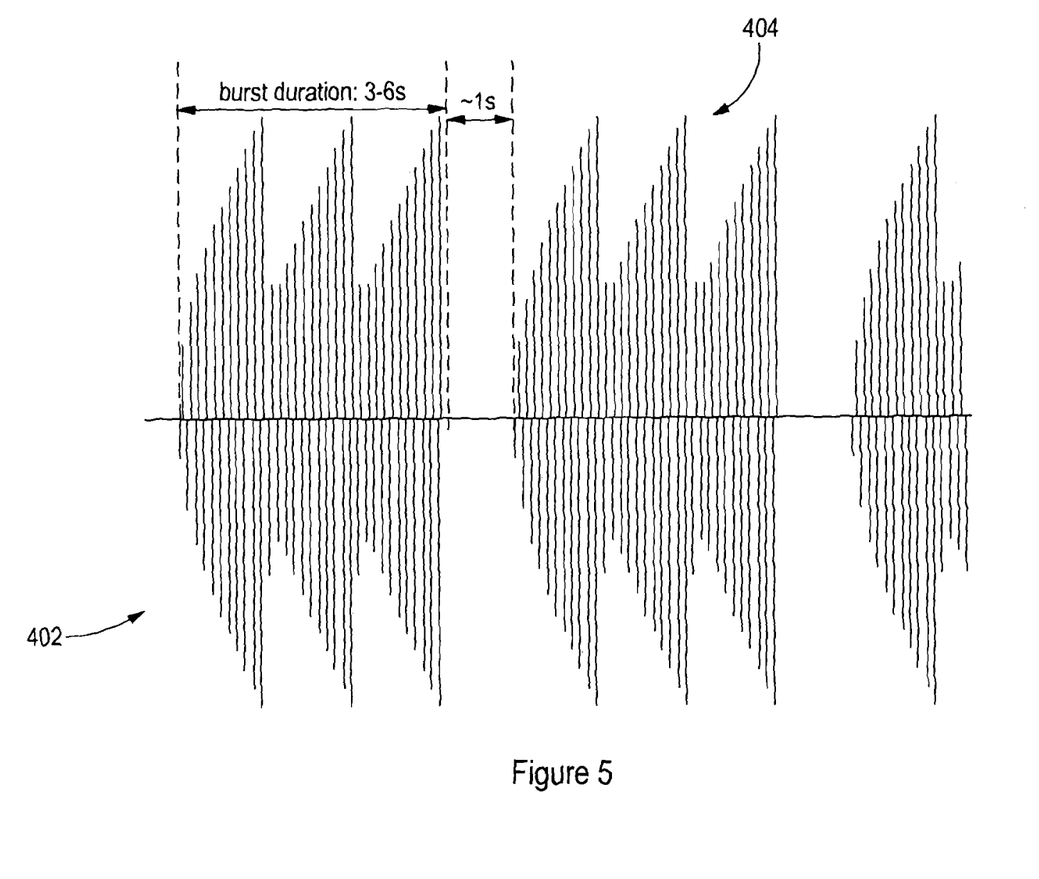
FIG. 5 is a graphical representation of a cycle of electrostimulation pulses according to a first embodiment of the present invention.

Finally, turning to FIG. 5, there is shown a graphical representation of a further alternative train of electrical pulses for applying to a subject to stimulate contraction of a target group of muscles, such as those of the lower leg. The pulses are represented as plots of voltage against time. The train of pulses represented in FIG. 5 comprises a first group of pulses 402 and a second group of pulses 404. The pulses in each of the first and second groups 402, 404 are arranged into sub-groups, each sub-group having a plurality of individual pulses therein. As can be seen, the sub-groups of pulses are arranged with an alternating polarity.

The individual pulses in the first and second groups 402, 404 are generally square in form, having a rapid increase in voltage from zero to a nominal voltage between 70 and 120 V, which is held for substantially the entire duration of the pulse, after which the voltage is rapidly decreased to zero. Peak voltages of up to 150 V may be applied, depending upon the intensity of the stimulation to be applied to the subject. A triangular wave voltage signal having a frequency of from 1.0 to 2.0 Hz, is applied to modulate the peak voltage of the individual pulses, as shown in FIG. 5. The modulation dept in the amplitude of the peak voltage of each pulse as shown in FIG. 4 is about 50%.

Each pulse has a width, that is a duration, of 1.0 millisecond. The pulses within each sub-group are separated by a first inter-pulse rest period of 100 microseconds.

Further, successive groups of pulses are separated by a second rest period. The second rest period is 25 milliseconds.

As shown in FIG. 5, the first group 402 and the second group 404 are separated by a third rest period. In this embodiment, the third rest period between successive groups of pulses is up to 3.0 seconds.

The train of pulses represented in FIG. 5 are operated at a duty cycle of from 20 to 50%.

The pulse train shown in FIG. 5 is repeatedly applied to the subject, as described above, during a treatment session.

The invention claimed is:

1. A method of increasing the blood flow in a subject by the electrostimulation of the muscles of the subject, the method comprising applying to the subject a plurality electrical pulses to induce contraction of at least one muscle of the subject, each pulse having a pulse width of at least 0.5 milliseconds; wherein the amplitude of the waveform of the pulses provided by the generator is modulated and the frequency of the modulation is up to 4 Hz; further wherein the plurality of pulses is provided in groups, each group comprising two or more pulses separated by a first inter-pulse rest period, the groups being separated by a second inter-pulse rest period, wherein the first inter-pulse rest period is from 50 to 250 microseconds.

2. The method according to claim 1, wherein the electrical pulses are applied transcutaneously to the subject.

3. The method according to claim 1, wherein the pulse width is greater than 0.75 milliseconds.

4. The method according to claim 1, wherein the pulse width is no greater than 1.75 milliseconds.

5. The method according to claim 1, wherein each group of pulses comprises fewer than 10 pulses.

6. The method according to claim 1, wherein the second inter-pulse rest period is at least 10 milliseconds.

7. The method according to claim 1, wherein the train of pulses has a duty cycle of from 5 to 75%.

8. The method according to claim 1, wherein the stimulation intensity is from 10 to 50% of maximum voluntary contraction strength.

9. An apparatus for increasing the blood flow in a subject by the electrostimulation of the muscles of the subject, the apparatus comprising:

a generator for generating a plurality of electrical pulses;

means for applying the electrical pulses to the subject to induce contraction of at least one muscle of the subject;

wherein the generator is operable to produce a plurality of electrical pulses each having a pulse width of at least 0.5 milliseconds;

wherein the amplitude of the waveform of the pulses provided by the generator is modulated and the frequency of the modulation is up to 4 Hz;

wherein the generator is operable to provide pulses in groups, each group comprising two or more pulses separated by a first inter-pulse rest period, the groups being separated by a second inter-pulse rest period, wherein the first inter-pulse rest period is from 50 to 250 microseconds.

* * * * *